(12) United States Patent
Devin-Baudoin et al.

(10) Patent No.: US 7,138,109 B2
(45) Date of Patent: Nov. 21, 2006

(54) USE OF PARTICULAR AMINOSILICONES AS A PRE-OR POST-TREATMENT OF PROCESSES FOR BLEACHING KERATIN FIBRES

(75) Inventors: Priscille Devin-Baudoin, Vanves (FR); Anne Sabbagh, Rueil Malmaison (FR)

(73) Assignee: L'Oreal, SA (FR)

( * ) Notice: Subject to any disclaimer, the term of this patent is extended or adjusted under 35 U.S.C. 154(b) by 555 days.

(21) Appl. No.: 10/290,341

(22) Filed: Nov. 8, 2002

(65) Prior Publication Data

US 2003/0129155 A1 Jul. 10, 2003

(30) Foreign Application Priority Data

Nov. 8, 2001 (FR) .................................. 01 14468

(51) Int. Cl.
*A61Q 5/08* (2006.01)
(52) U.S. Cl. ................... 424/62; 424/70.12; 424/70.22
(58) Field of Classification Search .................... None
See application file for complete search history.

(56) References Cited

U.S. PATENT DOCUMENTS

| | | | |
|---|---|---|---|
| 2,047,398 A | 7/1936 | Voss et al. |
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,723,248 A | 11/1955 | Wright |
| 2,781,354 A | 2/1957 | Mannheimer |
| 2,798,053 A | 7/1957 | Brown |
| 2,923,692 A | 2/1960 | Ackerman et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,578 A | 6/1971 | Kamphausen |
| 3,632,559 A | 1/1972 | Matter et al. |
| 3,810,977 A | 5/1974 | Levine et al. |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,990,459 A | 11/1976 | Papantoniou |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,070,533 A | 1/1978 | Papantoniou et al. |
| 4,075,136 A | 2/1978 | Schaper |
| 4,076,912 A | 2/1978 | Papantoniou et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,157,388 A | 6/1979 | Christiansen |
| 4,165,367 A | 8/1979 | Chakrabarti |
| 4,172,887 A | 10/1979 | Vanlerberghe et al. |
| 4,217,914 A | 8/1980 | Jacquet et al. |
| 4,223,009 A | 9/1980 | Chakrabarti |
| 4,237,243 A | 12/1980 | Quack et al. |
| 4,277,581 A | 7/1981 | Vanlerberghe et al. |
| 4,282,203 A | 8/1981 | Jacquet et al. |
| 4,349,532 A | 9/1982 | Vanlerberghe et al. |
| 4,509,949 A | 4/1985 | Huang et al. |
| 4,591,610 A | 5/1986 | Grollier |
| 4,608,250 A | 8/1986 | Jacquet et al. |
| 4,673,568 A | 6/1987 | Grollier et al. |
| 4,693,935 A | 9/1987 | Mazurek |
| 4,702,906 A | 10/1987 | Jacquet et al. |
| 4,710,314 A | 12/1987 | Madrange et al. |
| 4,719,099 A | 1/1988 | Grollier et al. |
| 4,719,282 A | 1/1988 | Nadolsky et al. |

(Continued)

FOREIGN PATENT DOCUMENTS

| | | |
|---|---|---|
| AU | 200039428 | 2/2001 |
| DE | 197 54 053 | 6/1999 |
| EP | 0 227 994 | 9/1989 |
| EP | 0 342 834 | 11/1989 |
| EP | 0 486 135 | 5/1992 |

(Continued)

OTHER PUBLICATIONS

"Encyclopedia of Chemical Technology", Kirk-Othmer, Third Edition, 1982, vol. 15, pp. 439-458.
"Encyclopedia of Chemical Technology", Kirk-Othmer, Third Edition, 1982, vol. 22, pp. 332-433.

(Continued)

*Primary Examiner*—Jyothsna Venkat
(74) *Attorney, Agent, or Firm*—Finnegan, Henderson, Farabow, Garrett & Dunner LLP

(57) ABSTRACT

The use, as a pre- or post-treatment of a process for bleaching keratin fibres, such as human hair, of a composition comprising at least one particular aminosilicone as defined herein.

Processes for bleaching keratin fibres, such as hair, comprising a pre- or post-treatment with a composition comprising at least one particular aminosilicone as defined herein.

56 Claims, No Drawings

U.S. PATENT DOCUMENTS

| | | | |
|---|---|---|---|
| 4,728,571 | A | 3/1988 | Clemens et al. |
| 4,761,273 | A | 8/1988 | Grollier et al. |
| 4,770,873 | A | 9/1988 | Wolfram et al. |
| 4,839,166 | A | 6/1989 | Grollier et al. |
| 4,957,732 | A | 9/1990 | Grollier et al. |
| 4,972,037 | A | 11/1990 | Garbe et al. |
| 4,996,059 | A | 2/1991 | Grollier et al. |
| 5,009,880 | A | 4/1991 | Grollier et al. |
| 5,057,311 | A | 10/1991 | Kamegai et al. |
| 5,061,289 | A | 10/1991 | Clausen et al. |
| 5,077,040 | A | 12/1991 | Bergmann et al. |
| 5,085,860 | A | 2/1992 | Junino et al. |
| 5,089,252 | A | 2/1992 | Grollier et al. |
| 5,106,612 | A | 4/1992 | Maignan et al. |
| 5,139,037 | A | 8/1992 | Grollier et al. |
| 5,154,918 | A | 10/1992 | Maignan et al. |
| 5,196,189 | A | 3/1993 | Jacquet et al. |
| 5,210,324 | A | 5/1993 | Farrar et al. |
| 5,340,367 | A | 8/1994 | Schultz et al. |
| 5,344,464 | A | 9/1994 | Madrange et al. |
| 5,380,340 | A | 1/1995 | Neunhoeffer et al. |
| 5,466,878 | A | 11/1995 | Junino et al. |
| 5,534,267 | A | 7/1996 | Neunhoeffer et al. |
| 5,538,717 | A | 7/1996 | De La Poterie |
| 5,583,257 | A | 12/1996 | Junino et al. |
| 5,626,840 | A | 5/1997 | Thomaides et al. |
| 5,663,366 | A | 9/1997 | Neunhoeffer et al. |
| 5,708,151 | A | 1/1998 | Mockli |
| 5,741,337 | A | 4/1998 | Bone et al. |
| 5,756,076 | A | 5/1998 | Cervantes et al. |
| 5,766,576 | A | 6/1998 | Lowe et al. |
| 5,773,611 | A | 6/1998 | Zysman et al. |
| 5,833,997 | A | 11/1998 | Mahieu et al. |
| 5,925,341 | A | 7/1999 | Cervantes et al. |
| 5,958,392 | A | 9/1999 | Grollier et al. |
| 5,976,195 | A | 11/1999 | De La Mettrie et al. |
| 6,010,541 | A | 1/2000 | De La Mettrie |
| 6,071,504 | A | 6/2000 | Kawai et al. |
| 6,099,592 | A | 8/2000 | Vidal et al. |
| 6,099,593 | A | 8/2000 | Terranova et al. |
| 6,143,286 | A | 11/2000 | Bhambhani et al. |
| 6,177,090 | B1 | 1/2001 | Dubief et al. |
| 6,179,881 | B1 | 1/2001 | Henrion et al. |
| 6,214,326 | B1 | 4/2001 | Dupuis |
| 6,254,646 | B1 | 7/2001 | De La Mettrie et al. |
| 6,260,556 | B1 * | 7/2001 | Legrand et al. ............. 132/208 |
| 6,284,003 | B1 | 9/2001 | Rose et al. |
| 6,319,959 | B1 | 11/2001 | Mougin et al. |
| 6,372,876 | B1 | 4/2002 | Kim et al. |
| 6,395,265 | B1 | 5/2002 | Mougin et al. |
| 6,471,953 | B1 | 10/2002 | N'Guyen et al. |
| 6,479,042 | B1 | 11/2002 | Nguyen et al. |
| 6,506,373 | B1 | 1/2003 | Dannecker et al. |
| 6,511,669 | B1 | 1/2003 | Garnier et al. |
| 6,582,477 | B1 | 6/2003 | Plos |
| 6,613,313 | B1 | 9/2003 | Kimura |
| 6,770,271 | B1 | 8/2004 | Mondet et al. |
| 6,824,764 | B1 * | 11/2004 | Devin-Baudoin et al. .. 424/70.1 |
| 6,824,765 | B1 * | 11/2004 | Gawtrey et al. ........... 424/70.1 |
| 6,846,333 | B1 | 1/2005 | Legrand et al. |
| 6,916,467 | B1 | 7/2005 | Devin-Baudoin et al. |
| 2002/0006389 | A1 | 1/2002 | Restle et al. |
| 2002/0187117 | A1 | 12/2002 | Devin-Baudoin et al. |

FOREIGN PATENT DOCUMENTS

| | | |
|---|---|---|
| EP | 0 412 707 | 2/1994 |
| EP | 0 582 152 | 2/1994 |
| EP | 0 646 572 | 4/1995 |
| EP | 0 890 355 | 1/1999 |
| EP | 0 412 704 | 4/1999 |
| GB | 0 839 805 | 6/1960 |
| GB | 0 922 457 | 4/1963 |
| GB | 1 021 400 | 3/1966 |
| GB | 1 026 978 | 4/1966 |
| GB | 1 153 196 | 5/1969 |
| GB | 1 486 576 | 9/1977 |
| GB | 1 546 809 | 5/1979 |
| GB | 2 141 454 | 12/1984 |
| GB | 2 165 550 | 4/1986 |
| GB | 2 058 103 | 4/1991 |
| JP | 2001-10935 | 1/2001 |
| WO | WO 93/23446 | 11/1993 |
| WO | WO 94/07844 | 4/1994 |
| WO | WO 94/10131 | 5/1994 |
| WO | WO 94/24097 | 10/1994 |
| WO | WO 95/00578 | 1/1995 |
| WO | WO 95/01772 | 1/1995 |
| WO | WO 95/15144 | 6/1995 |
| WO | WO 95/16665 | 6/1995 |

OTHER PUBLICATIONS

"Encyclopedia of Chemical Technology", Kirk-Othmer, Third Edition, 1982, vol. 3, pp. 896-900.
"Industrial Gums—Polysaccharides and their Derivatives", edited by Roy L. Whistler, Second Edition, Academic Press.
"Polymers in Nature", E.A. MacGregor & C.T. Greenwood, John Wiley & Sons, Chapter 6, pp. 240-328, 1980.
"Volatile Silicone Fluids for Cosmetic Formulations", Cosmetics and Toiletries, vol. 91, Jan. 1976, pp. 27-32.
Copending U.S. Appl. No. 10/290,149, filed Nov. 8, 2002.
Copending U.S. Appl. No. 10/290,159, filed Nov. 8, 2002.
Copending U.S. Appl. No. 10/290,189, filed Nov. 8, 2002.
Copending U.S. Appl. No. 10/290,192, filed Nov. 8, 2002.
Copending U.S. Appl. No. 10/290,208, filed Nov. 8, 2002.
Copending U.S. Appl. No. 10/290,226, filed Nov. 8, 2002.
Copending U.S. Appl. No. 10/290,342, filed Nov. 8, 2002.
Copending U.S. Appl. No. 10/290,343, filed Nov. 8, 2002.
Copending U.S. Appl. No. 10/290,345, filed Nov. 8, 2002.
Copending U.S. Appl. No. 10/290,348, filed Nov. 8, 2002.
Copending U.S. Appl. No. 10/290,372, filed Nov. 8, 2002.
Copending U.S. Appl. No. 10/290,409, filed Nov. 8, 2002.
Copending U.S. Appl. No. 11/158,014, filed Jun. 22, 2005.
English language Derwent Abstract of DE 42 29 922, Mar. 10, 1994.
English language Derwent Abstract of DE 44 02 929, Jun. 22, 1995.
English language Derwent Abstract of DE 44 20 736, Aug. 10, 1995.
English language Derwent Abstract of DE 44 24 530, Jan. 18, 1996.
English language Derwent Abstract of DE 44 24 533, Jan. 18, 1996.
English language Derwent Abstract of EP 0 080 976, Jun. 8, 1983.
English language Derwent Abstract of EP 0 122 324, Oct. 24, 1984.
English language Derwent Abstract of EP 0 225 261, Jun. 10, 1987.
English language Derwent Abstract of EP 0 368 763, May 16, 1990.
English language Derwent Abstract of EP 0 765 655, Apr. 2, 1987.
English language Derwent Abstract of FR 2 679 448, Jan. 29, 1993.
English language Derwent Abstract of FR 2 679 558, Jan. 29, 1993.
English language Derwent Abstract of JP 2001-10936, Jan. 16, 2001.
English language Derwent Abstract of JP 2-250814, Oct. 8, 1990.
English language Derwent Abstract of JP 4-154713, May 27, 1992.
English language Derwent Abstract of JP 8-157340, Jun. 18, 1996.
English language Derwent Abstract of JP 9-151120, Jun. 10, 1997.
English language JAPIO Abstract of JP 2-019576, Jan. 23, 1990.
English language JAPIO Abstract of JP 9-110659, Apr. 28, 1997.
French Search Report for FR 0 114 468, dated Aug. 8, 2002.
French Search Report for FR 0 114 469, dated Aug. 22, 2002.
French Search Report for FR 0 114 470, dated Sep. 18, 2002.
French Search Report for FR 0 114 472, dated Aug. 30, 2002.
French Search Report for FR 0 114 473, dated Sep. 16, 2002.
French Search Report for FR 0 114 474, dated Aug. 8, 2002.
French Search Report for FR 0 114 476, dated Sep. 20, 2002.
French Search Report for FR 0 114 477, dated Sep. 20, 2002.
French Search Report for FR 0 114 478, dated Sep. 18, 2002.
French Search Report for FR 0 114 479, dated Sep. 16, 2002.

French Search Report for FR 0 114 480, dated Aug. 9, 2002.
French Search Report for FR 0 114 481, dated Sep. 4, 2002.
French Search Report for FR 0 114 482, dated Aug. 28, 2002.
French Search Report for FR 0 114 484, dated Sep. 4, 2002.
French Search Report for FR 0 114 485, dated Aug. 29, 2002.
French Search Report for FR 0 114 486, dated Sep. 23, 2002.
P.D. Dorgan "Waxes in Cosmetics", Drug and Cosmetic Industry, Dec. 1983, pp. 30-33.
Porter, M.R., Handbook of Surfactants 116-178 (Blackie & Son 1991).
English language Patent Abstract of Japan of JP 2001-10935, Jan. 16, 2001.
Office Action in co-pending U.S. Appl. No. 10/290,149, dated Apr. 30, 2004.
Office Action in co-pending U.S. Appl. No. 10/290,149, dated Nov. 4, 2004.
Office Action in co-pending U.S. Appl. No. 10/290,159, dated Dec. 27, 2004.
Office Action in co-pending U.S. Appl. No. 10/290,159, dated May 3, 2004.
Office Action in co-pending U.S. Appl. No. 10/290,189, dated Feb. 16, 2006.
Office Action in co-pending U.S. Appl. No. 10/290,192, dated Jan. 11, 2006.
Office Action in co-pending U.S. Appl. No. 10/290,208, dated Jan. 11, 2006.
Office Action in co-pending U.S. Appl. No. 10/290,342, dated Jan. 25, 2006.
Office Action in co-pending U.S. Appl. No. 10/290,343, dated Jan. 25, 2006.
Office Action in co-pending U.S. Appl. No. 10/290,345, dated Feb. 9, 2006.
Office Action in co-pending U.S. Appl. No. 10/290,372, dated Jan. 10, 2006.
English language Derwent Abstract of DE 197 54 053, Jun. 10, 1999.

* cited by examiner

USE OF PARTICULAR AMINOSILICONES AS A PRE-OR POST-TREATMENT OF PROCESSES FOR BLEACHING KERATIN FIBRES

This disclosure relates to the use, as a pre- or post-treatment of a process for bleaching keratin fibres, such as human hair, of a composition comprising at least one aminosilicone, as defined herein.

This disclosure also relates to processes for bleaching keratin fibres, such as human hair, comprising a pre- or post-treatment with a composition comprising at least one aminosilicone as defined herein.

Natural shades of dark hair may be lightened, for example, in a long-lasting manner though the use of at least one bleaching treatment. Artificial shades obtained through the use of at least one direct dye and/or at least one oxidation dye may also be lightened, for example, through the use of at least one bleaching treatment.

A bleaching composition used in these treatments may comprise ready-to-use thickened aqueous hydrogen peroxide compositions. A bleaching composition may be chosen, for example, from anhydrous products (powders and creams) comprising alkaline compounds (amines and alkaline silicates), and peroxygenated oxidizing reagents, such as ammonium and alkali metal persulphates, perborates and percarbonates, which may be diluted at the time of use with aqueous hydrogen peroxide.

These oxidizing treatments may cause sensitization of the hair; for example, the hair may become drier and more difficult to disentangle, with a coarser feel.

A bleaching treatment may also be chosen, for example, from ready-to-use compositions comprising at least one anhydrous product (e.g., a powder or a cream) comprising at least one reducing agent, which may be mixed at the time of use with an aqueous composition optionally comprising a pH agent. A composition comprising at least one reducing agent may cause sensitization of the hair.

To improve the condition of hair fibres after a bleaching treatment, at least one rinse-out or at least one leave-in care product chosen from conditioners, treating masks, treating creams and sera have been used, for example.

These care products have at least the drawback of being temporary and requiring reapplication each time the hair is washed.

They may make the hair lank, rendering it lifeless with an unnatural slippery coated feel.

There is thus a need to improve the condition of the hair after a bleaching treatment.

After considerable research, the inventors have discovered, surprisingly and unexpectedly, that the use, as a pre- or post-treatment on keratin fibres, such as human hair, of a composition comprising at least one aminosilicone as defined herein, solves at least one of the problems mentioned above.

A new embodiment relates to the use, as a pre- or post-treatment of a process for bleaching keratin fibres, such as human hair, of a composition comprising at least one aminosilicone chosen from formulae (I) and (II).

In another embodiment, the use may, for example, improve the condition of the fibres after bleaching. The fibres may, for example, become softer, smooth from the root to the end, individualized, light, supple and silky. The fibre may feel, for example, much more natural than when a prior art conditioner is used after a bleaching operation. The hair may disentangle well and style more easily. The treatment may also avoid modifying the lightening power of the bleaching treatment. At least one cosmetic effect may be long-lasting and/or visible for a long period of time, such as at least six weeks.

The phrase "improvement in the condition of the fibre" means, for example, a reduction in the porosity and/or the alkaline solubility of the fibre and a potential improvement in the cosmetic properties, such as smoothness, softness and ease of disentangling and of styling.

This effect may be remanent, e.g., long-lasting.

The porosity may be measured by fixing at 37° C. and at pH 10, for two minutes, 2-nitro-para-phenylenediamine at 0.25% in an ethanol/pH. 10 buffer mixture (10/90 volume ratio).

The alkaline solubility may correspond to the loss of mass of a sample of 100 mg of keratin fibres under the action of decinormal sodium hydroxide for 30 minutes at 65° C.

Another new embodiment relates to a bleaching process comprising: applying to keratin fibres, such as human hair, which may be wet or dry, washed or unwashed, a composition comprising at least one aminosilicone chosen from formulae (I) and (II); leaving the composition to act at room temperature or with a supply of heat; optionally rinsing the fibres; applying a bleaching composition; optionally washing the fibres; optionally rinsing the fibres; and optionally drying them.

Another new embodiment relates to a bleaching process comprising: applying a bleaching composition to keratin fibres, such as human hair; washing the fibres with shampoo; rinsing them with water; applying a composition comprising at least one aminosilicone chosen from formulae (I) and (II) to the wet or dry fibres; leaving the composition to act at room temperature or with a supply of heat; optionally rinsing the fibres; and optionally drying them. In another embodiment, the composition may be applied, for example, to the fibres immediately after bleaching or after an interval.

Aminosilicone(s)

The at least one aminosiliconeis chosen from formulae (I) and (II):

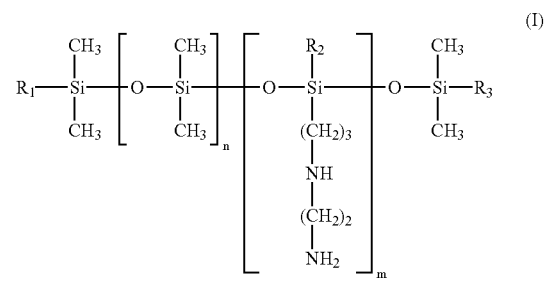

wherein:

m and n are numbers with a sum (n+m) ranging, for example, from 1 to 1000, and further, for example, 50 to 250, and still further, for example, from 100 to 200;

n is a number ranging from 0 to 999, for example from 49 to 249, and further, for example, from 125 to 175, and m is a number ranging from 1 to 1000, for example, 1 to 10, and further, for example, from 1 to 5;

$R_1$, $R_2$ and $R_3$, which may be identical or different, are chosen from a hydroxyl radical and C1–C4 alkoxy radicals, wherein at least one of the radicals $R_1$ to $R_3$ is chosen from alkoxy radicals.

For example, the alkoxy radical may be a methoxy radical.

The hydroxyl/alkoxy molar ratio may range, for example, from 0.2:1 to 0.4:1, for example, from 0.25:1 to 0.35:1, and further, for example, may be 0.3:1.

The at least one aminosilicone of formula (I) may have a weight-average molecular mass ranging, for example, from 2000 to 1 000 000, such as from 3500 to 200 000.

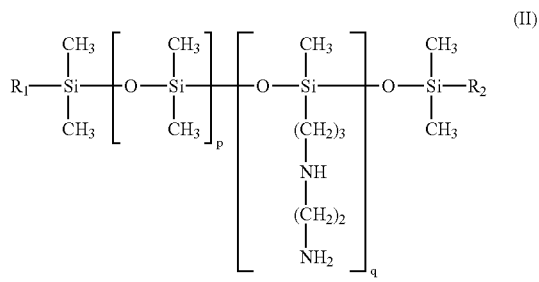

wherein:

p and q are numbers with a sum (p+q) ranging, for example, from 1 to 1000, for example, from 50 to 350 and further, for example, from 150 to 250;

p is a number ranging from 0 to 999, for example from 49 to 349, and further, for example, from 159 to 239, and q is a number ranging from 1 to 1000, for example, from 1 to 10, and further, for example, from 1 to 5;

$R_1$ and $R_2$, which are different, are chosen from a hydroxyl radical and C1–C4 alkoxy radicals, wherein at least one of the radicals $R_1$ and $R_2$ is chosen from alkoxy radicals.

For example, the alkoxy radical may be a methoxy radical.

The hydroxyl/alkoxy molar ratio may range, for example, from 1:0.8 to 1:1.1, for example, from 1:0.9 to 1:1, and further, for example, may be 1:0.95.

The at least one aminosilicone of formula (II) may have, for example, a weight-average molecular mass ranging from 2000 to 200 000, for example, from 5000 to 100 000, and further, for example, from 10 000 to 50 000.

The weight-average molecular mass of the at least one aminosilicone is measured by Gel Permeation Chromatography (GPC) at room temperature, as polystyrene equivalents. The columns used are styragel μ columns. The eluent is THF and the flow rate is 1 ml/minute. 200 μl of a solution at 0.5% by weight of silicone in THF are injected. The detection is performed by refractometry and UV-metry.

At least one commercial product comprising at least one aminosilicone chosen from formulae (I) and (II) may further comprise at least one aminosilicone other than those of formulae (I) and (II).

A product comprising at least one aminosilicone of structure (I) is sold, for example, by the company Wacker under the name Belsil ADM 652®.

A product comprising at least one aminosilicone of structure (II) is sold, for example, by the company Wacker under the name Fluid WR 1300®.

In another new embodiment, the at least one aminosilicone may be in the form of an oil-in-water emulsion. The oil-in-water emulsion may comprise at least one surfactant. The at least one surfactant may be chosen, for example, from cationic surfactants and non-ionic surfactants.

The aminosilicone particles in the emulsion may have a mean size ranging, for example, from 3 to 500 nanometres. Such particle sizes are measured with a laser granulometer.

For example, for the at least one aminosilicone of formula (II), microemulsions may range in size from 5 to 60 nanometres, for example, from 10 to 50 nanometres.

Microemulsions of the at least one aminosilicone of formula (II) are sold, for example, under the name Finish CT 96 E® or SLM 28020® by the company Wacker.

The aminosilicone chosen from formulae (I) and (II) may be chosen, for example, such that the contact angle with water of a hair treated with a composition comprising 2% AM (active materials) of the at least one aminosilicone ranges from 90 to 180°, for example from 90 to 130°.

A composition comprising at least one aminosilicone chosen from formulae (I) and (II) may be chosen, for example, such that the contact angle of a hair treated with the composition ranges from 90 to 180°, for example, from 90 to 130°.

The contact angle measurement is based on immersing a hair in distilled water. It consists in evaluating the force exerted by the water on the hair during its immersion in distilled water and during its removal. The forces thus measured are directly linked to the contact angle θ between the water and the surface of the hair. The hair is said to be hydrophilic when the angle θ ranges from 0 to less than 90°, and hydrophobic when this angle ranges from 90 to 180°, limits included.

The test is carried out with locks of natural hair that have been bleached under the same conditions and then washed.

Each 1 gram lock is placed in a crystallizing dish 75 mm in diameter and then covered uniformly with 5 ml of the test formulation. The lock is left for 15 minutes at room temperature and then rinsed for 30 seconds. The drained lock is left in the open air until it is completely dry.

For each evaluation, 10 hairs that have undergone the same treatment are analysed. Each sample, attached to a precision microbalance, is immersed via its end in a container filled with distilled water. This DCA balance ("Dynamic Contact Angle Analyser"), from the company Cahn Instruments, allows the force (F) exerted by the water on the hair to be measured.

In parallel, the perimeter (P) of the hair is measured by means of observation by microscope.

The mean wettability force on 10 hairs and the cross section of the analysed hairs make it possible to obtain the contact angle of the hair on the water according to the formula:

$$F = P * \lceil lv * \cos \theta$$

where F is the wettability force expressed in newtons, P is the perimeter of the hair in metres, ⌈lv is the liquid/water vapour interface tension in J/m² and θ is the contact angle.

The product SLM 28020® from Wacker at 12% in water (i.e., 2% active materials) gives a contact angle of 93° according to the test indicated above.

The at least one aminosilicone chosen from formulae (I) and (II) may be present, for example, in a pre- or post-treatment composition, in an amount ranging from 0.01% to 20% by weight, relative to the total weight of the composition. This amount may range, for example, from 0.1% to 15% by weight, such as from 0.5% to 10% by weight.

A pre- or post-treatment composition may comprise, for example, any ingredient used in cosmetics, for example, the art of haircare. The pre- or post-treatment composition may comprise, for example, at least one surfactant and/or at least one polymer. The at least one surfactant and/or at least one polymer may be selected from, for example, nonionic, cationic, anionic and amphoteric compounds. The at least one polymer may be chosen, for example, from aminosilicones other than those of formulae (I) and (II).

A pre- or post-treatment composition may have, for example, a pH ranging from 2 to 11, such as from 4 to 9, when it is in aqueous form.

A pre- or post-treatment composition may be in a form chosen from, for example, lotions, gels, creams, shampoos, sticks, mousses and sprays. At least one of these forms may be packed in a form chosen from pump-dispenser bottles and aerosol containers. If in the form of an aerosol, for example, the composition may further comprise at least one propellant chosen from, for example, alkanes dimethyl ether, nitrogen, nitrous oxide, carbon dioxide, haloalkanes, and mixtures thereof.

Another new embodiment comprises the pre- or post-treatment composition in the form of a shampoo.

The composition may comprise, for example, at least one surfactant, such as an anionic surfactant. The composition may comprise at least one anionic surfactant and, for example, at least one surfactant chosen from nonionic surfactants and amphoteric surfactants The post-treatment composition may be applied, for example, immediately after bleaching, or after an interval. The phrase "after an interval" means, for example, an application performed a few hours, one day or several days (e.g., from 1 to 60 days) after bleaching.

Several applications may occur, for example, between bleaching operations.

The number of applications between bleaching operations may range, for example, from 1 to 60, and further, for example, from 2 to 30.

A pre- or post-treatment composition may be used, for example, in rinse-out or leave-in mode, e.g., its application may or may not be followed by a rinsing operation.

If the application is followed by rinsing, the acting time of the pre- or post-treatment composition ranges, for example, from a few seconds to 60 minutes, such as from 30 seconds to 15 minutes.

The application temperature of the pre- or post-treatment composition may range, for example, from 10 to 70° C. The application temperature may range, for example, from 20 to 60° C., such as at room temperature.

Illustrative, non-limiting examples follow.

EXAMPLES

The following three compositions were prepared. (expressed as grams of Active Material)

| Composition A | | |
|---|---|---|
| Polydimethylsiloxane of formula (I), sold under the name Belsil ADM 652 ® by the company Wacker | | 2 |
| Cyclopentadimethylsiloxane | qs | 100 |
| Composition B | | |
| Polydimethylsiloxane of formula (II), sold under the name SLM 28020 ® by the company Wacker | | 2 |
| Demineralized water | qs | 100 |
| Composition C | | |
| Cetylstearyl alcohol/sodium lauryl sulphate/cetyl myristate/myristyl alcohol (62/20/8/10) | | 12 |
| Oxyethylenated (20 EO) oleyl alcohol | | 0.1 |
| Glycerol | | 0.5 |
| Polydimethylsiloxane of formula (I), sold under the name Belsil ADM 652 by the company Wacker | | 2 |
| Demineralized water | qs | 100 |

Compositions A, B and C were each applied to natural chestnut-brown hair:
1/ as a pre-treatment to an oxidizing bleaching operation using the commercial product Platifiz® from the company L'Oréal;
2/ as a post-treatment to an oxidizing bleaching operation using the commercial product Platifiz® from the company L'Oréal.

In pre-treatment, the hair was thus treated with these compositions A, B and C for 30 minutes at a temperature of 37° C., washed with water, bleached with Platifiz® and rinsed again thoroughly before drying.

As a post-treatment, the hair was bleached with Platifiz® and rinsed with water before being treated with compositions A, B and C, and then rinsed again thoroughly before being dried.

After these treatments, the hair was smoother, softer and easier to disentangle than in the absence of a pre- or post-treatment.

In addition, the level of bleaching was not altered by the treatments.

What is claimed is:

1. A process for at least one of pre-treating and post-treating keratin fibres in a bleaching process using at least one bleaching composition, comprising applying to the keratin fibres a pretreatment or post-treatment composition comprising at least one aminosilicone chosen from formulae (I) and (II):

$$R_1-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n-\left[\underset{\underset{(CH_2)_3}{|}}{\overset{\overset{R_2}{|}}{Si}}-O\right]_m-\underset{\underset{CH_3}{|}}{\overset{\overset{CH_3}{|}}{Si}}-R_3 \quad (I)$$

with side chain $(CH_2)_3-NH-(CH_2)_2-NH_2$ wherein:
m and n are numbers with a sum (n+m) ranging from 1 to 1000, n is a number ranging from 0 to 999, and m is a number ranging from 1 to 1000; and
$R_1$, $R_2$ and $R_3$, which may be identical or different, are chosen from a hydroxyl radical and C1–C4 alkoxy radicals, wherein at least one of the radicals $R_1$ to $R_3$ is chosen from alkoxy radicals;

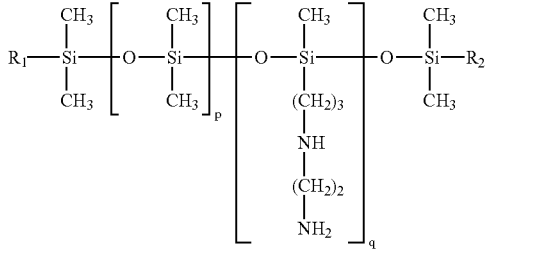

wherein:
p and q are numbers with a sum (p+q) ranging from 1 to 1000,
p is a number ranging from 0 to 999, and q is a number ranging from 1 to 1000; and R₁ and R₂, which are different, are chosen from a hydroxyl radical and $C_{1-C4}$ alkoxy radicals, wherein at least one of the radicals R₁ and R₂ is chosen from alkoxy radicals.

2. The process according to claim 1, wherein the keratin fibres are hair.

3. The process according to claim 1, wherein the sum (m+n) ranges from 50 to 250.

4. The process according to claim 1, wherein the sum (m+n) ranges from 100 to 200.

5. The process according to claim 1, wherein n ranges from 49 to 249.

6. The process according to claim 1, wherein n ranges from 125 to 175.

7. The process according to claim 1, wherein m ranges from 1 to 10.

8. The process according to claim 1, wherein m ranges from 1 to 5.

9. The process according to claim 1, wherein the sum (p+q) ranges from 50 to 350.

10. The process according to claim 1, wherein the sum (p+q) ranges from 150 to 250.

11. The process according to claim 1, wherein p ranges from 49 to 349.

12. The process according to claim 1, wherein p ranges from 159 to 239.

13. The process according to claim 1, wherein q ranges from 1 to 10.

14. The process according to claim 1, wherein q ranges from 1 to 5.

15. The process according to claim 1, wherein the $C_1$–$C_4$ alkoxy radical is a methoxy radical.

16. The process according to claim 1, wherein the at least one aminosilicone is chosen from formula (I) and has a hydroxyl/alkoxy molar ratio ranging from 0.2:1 to 0.4:1.

17. The process according to claim 1, wherein the at least one aminosilicone is chosen from formula (I) and has a hydroxyl/alkoxy molar ratio ranging from 0.25:1 to 0.35:1.

18. The process according to claim 1, wherein the at least one aminosilicone is chosen from formula (I) and has a hydroxyl/alkoxy molar ratio of 0.3:1.

19. The process according to claim 1, wherein the at least one aminosilicone is chosen from formula (II) and has a hydroxyl/alkoxy molar ratio ranging from 1:0.8 to 1:1.1.

20. The process according to claim 1, wherein the at least one aminosilicone is chosen from formula (II) and has a hydroxyl/alkoxy molar ratio ranging from 1:0.9 to 1:1.

21. The process according to claim 1, wherein the at least one aminosilicone is chosen from formula (II) and has a hydroxyl/alkoxy molar ratio of 1:0.95.

22. The process according to claim 1, wherein the at least one aminosilicone is chosen from formula (I) and has a weight-average molecular mass ranging from 2000 to 1 000 000.

23. The process according to claim 22, wherein the at least one aminosilicone is chosen from formula (I) and has a weight-average molecular mass ranging from 3500 to 200 000.

24. The process according to claim 1, wherein the at least one aminosilicone is chosen from formula (II) and has a weight-average molecular mass ranging from 2000 to 200 000.

25. The process according to claim 24, wherein the at least one aminosilicone is chosen from formula (II) and has a weight-average molecular mass ranging from 5000 to 100 000.

26. The process according to claim 25, wherein the at least one aminosilicone is chosen from formula (II) and has a weight-average molecular mass ranging from 10 000 to 50 000.

27. The process according to claim 1, wherein the at least one aminosilicone is in the form of an oil-in-water emulsion and further comprises at least one surfactant.

28. The process according to claim 27, wherein the at least one surfactant is chosen from cationic and nonionic surfactants.

29. The process according to claim 28, wherein the particle size of the at least one aminosilicone in the emulsion ranges from 3 to 500 nanometres.

30. The process according to claim 29, wherein the particle size of the at least one aminosilicone in the emulsion ranges from 5 to 60 nanometres.

31. The process according to claim 30, wherein the particle size of the at least one aminosilicone in the emulsion ranges from 10 to 50 nanometres.

32. The process according to claim 1, wherein the at least one aminosilicone is chosen such that the contact angle with water of hair treated with a pretreatment or post-treatment composition comprising 2% AM (active materials) of said at least one aminosilicone ranges from 90 to 180°.

33. The process according to claim 32, wherein the at least one aminosilicone is chosen such that the contact angle with water of hair treated with a pretreatment or post-treatment composition comprising 2% AM (active materials) of said aminosilicone ranges from 90 to 130°.

34. The process according to claim 1, wherein the pretreatment or post-treatment composition comprising at least one aminosilicone is chosen such that a contact angle of hair treated with said pretreatment or post-treatment composition ranges from 90 to 180°.

35. The process according to claim 34, wherein the at least one aminosilicone is present in an amount ranging from 0.01% to 20% by weight, relative to the total weight of the pretreatment or post-treatment composition.

36. The process according to claim 35, wherein the at least one aminosilicone is present in an amount ranging from 0.1% to 15% by weight, relative to the total weight of the pretreatment or post-treatment composition.

37. The process according to claim 36, wherein the at least one aminosilicone is present in an amount ranging from 0.5% to 10% by weight, relative to the total weight of the pretreatment or post-treatment composition.

38. The process according to claim 1, wherein the pretreatment or post-treatment composition is in a form chosen from lotions, gels, creams, shampoos, sticks, mousses and sprays.

39. The process according to claim 1, wherein the pretreatment or post-treatment composition is packaged in a form chosen from pump-dispenser bottles and aerosol containers.

40. The process according to claim 39, wherein the pretreatment or post-treatment composition further comprises at least one propellant chosen from alkanes, dimethyl ether, nitrogen, nitrous oxide, carbon dioxide and haloalkanes.

41. The process according to claim 1, wherein the pretreatment or post-treatment composition further comprises at least one surfactant chosen from nonionic, cationic, anionic and amphoteric surfactants.

42. The process according to claim 41, wherein the pretreatment or post-treatment composition comprises at least one anionic surfactant and at least one surfactant chosen from nonionic and amphoteric surfactants.

43. The process according to claim 1, wherein the pretreatment or post-treatment composition comprises at least one polymer chosen from polymers other than the aminosilicones chosen from formulae (I) and (II).

44. The process according to claim 43, wherein the at least one polymer is chosen from nonionic, cationic, anionic and amphoteric polymers.

45. The process according to claim 44, wherein the at least one polymer is chosen from aminosilicones other than those of formulae (I) and (II).

46. The process according to claim 1, wherein the pretreatment or post-treatment composition has a pH ranging from 2 to 11.

47. The process according to claim 46, wherein the pH ranges from 4 to 9.

48. The process according to claim 1, wherein the process improves the condition of human keratin fibres after bleaching.

49. A process for bleaching keratin fibres comprising: (a) applying to the fibres a pretreatment composition comprising at least one aminosilicone chosen from formulae (I) and (II):

(b) optionally rinsing the fibres and optionally drying the fibres;
(c) applying a bleaching composition for a time sufficient to develop a color;
;
(e) optionally washing the fibres;
(f) optionally rinsing the fibres; and
(g) optionally drying the fibres.

50. The process according to claim 49, further comprising leaving the pretreatment composition for a time to act ranging from a few seconds to 60 minutes.

51. The process according to claim 50, wherein the time to act ranges from 30 seconds to 15 minutes.

52. A process for bleaching keratin fibres comprising:
(a) applying to the fibres a bleaching composition;
(b) leaving the bleaching composition to act for a time sufficient to bleach;
(c) optionally rinsing the fibres;
(d) optionally drying the fibres;
(e) applying to the fibres a post-treatment composition comprising at least one aminosilicone chosen from formulae (I) and (II):

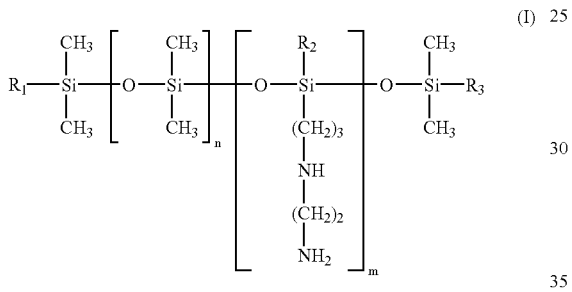

(I)

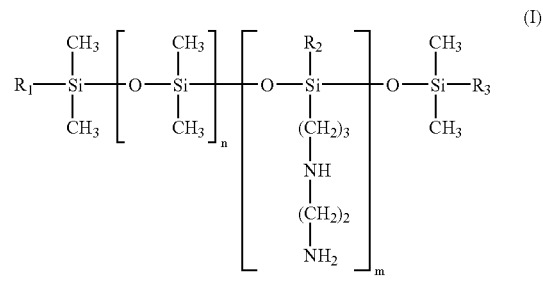

(I)

wherein:
m and n are numbers with a sum (n+m) ranging from 1 to 1000, n is a number ranging from 0 to 999, and m is a number ranging from 1 to 1000; and
$R_1$, $R_2$ and $R_3$, which may be identical or different, are chosen from a hydroxyl radical and C1–C4 alkoxy radicals, wherein at least one of the radicals $R_1$ to $R_3$ is chosen from alkoxy radicals;

wherein:
m and n are numbers with a sum (n+m) ranging from 1 to 1000, n is a number ranging from 0 to 999, and m is a number ranging from 1 to 1000; and
$R_1$, $R_2$ and $R_3$, which may be identical or different, are chosen from a hydroxyl radical and C1–C4 alkoxy radicals, wherein at least one of the radicals $R_1$ to $R_3$ is chosen from alkoxy radicals;

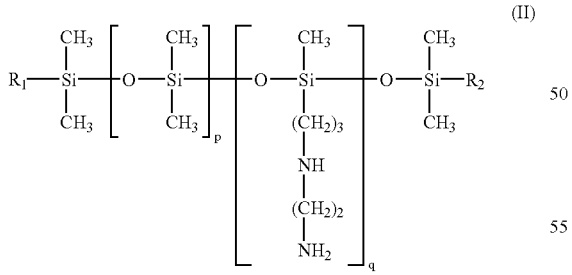

(II)

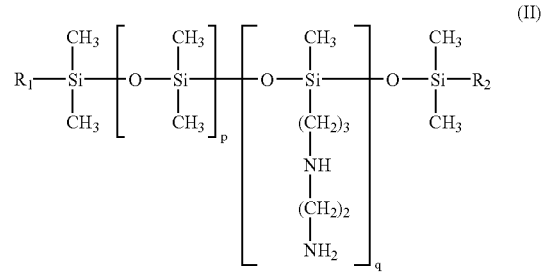

(II)

wherein:
p and q are numbers with a sum (p+q) ranging from 1 to 1000,
p is a number ranging from 0 to 999, and q is a number ranging from 1 to 1000; and
$R_1$ and $R_2$, which are different, are chosen from a hydroxyl radical and $C_1$–$C_4$ alkoxy radicals, wherein at least one of the radicals $R_1$ and $R_2$ is chosen from alkoxy radicals;

wherein:
p and q are numbers with a sum (p+q) ranging from 1 to 1000,
p is a number ranging from 0 to 999, and q is a number ranging from 1 to 1000; and
$R_1$ and $R_2$, which are different, are chosen from a hydroxyl radical and $C_1$–$C_4$ alkoxy radicals, wherein at least one of the radicals $R_1$ and $R_2$ is chosen from alkoxy radicals.

53. The process according to claim 52, comprising applying the post-treatment composition to the keratin fibres immediately after said time sufficient to bleach or after an interval following said time sufficient to bleach.

54. The process according to claim 52, comprising applying the post-treatment composition before applying to the fibres a subsequent bleaching composition.

55. The process according to claim 52, further comprising leaving the post-treatment composition for a time to act ranging from a few seconds to 60 minutes.

56. The process according to claim 55, wherein the time to act ranges from 30 seconds to 15 minutes.

* * * * *

UNITED STATES PATENT AND TRADEMARK OFFICE
CERTIFICATE OF CORRECTION

| | |
|---|---|
| PATENT NO. | : 7,138,109 B2 |
| APPLICATION NO. | : 10/290341 |
| DATED | : November 21, 2006 |
| INVENTOR(S) | : Priscille Devin-Baudoin et al. |

It is certified that error appears in the above-identified patent and that said Letters Patent is hereby corrected as shown below:

On the title page, item (54), line 2, "PRE-OR" should read --PRE- OR--.

In claim 1, column 6, line 46, "C1-C4" should read --$C_1$-$C_4$--.

In claim 1, column 7, line 2, "$C_{1-C4}$" should read --$C_1$-$C_4$--.

In claim 49, column 9, line 42, "C1-C4" should read --$C_1$-$C_4$--.

In claim 49, column 10, line 5, delete ";".

In claim 49, column 10, line 6, "(e)" should read --(d)--.

In claim 49, column 10, line 7, "(f)" should read --(e)--.

In claim 49, column 10, line 8, "(g)" should read --(f)--.

In claim 52, column 10, line 42, "C1-C4" should read --$C_1$-$C_4$--.

Signed and Sealed this

Third Day of April, 2007

JON W. DUDAS
*Director of the United States Patent and Trademark Office*